United States Patent [19]
Smith

[11] Patent Number: 6,089,103
[45] Date of Patent: Jul. 18, 2000

[54] METHOD OF FLOW MEASUREMENTS

[75] Inventor: Leif Smith, Uppsala, Sweden

[73] Assignee: Radi Medical Systems AB, Uppsala, Sweden

[21] Appl. No.: 09/073,061

[22] Filed: May 6, 1998

[51] Int. Cl.$^7$ .................................................... G01F 1/708
[52] U.S. Cl. ................................... 73/861.05; 73/861.95; 600/549; 600/486
[58] Field of Search ............................ 73/861.05, 861.95, 73/861.07; 600/549, 561, 573, 581, 485, 486

[56] References Cited

U.S. PATENT DOCUMENTS

| | | | |
|---|---|---|---|
| 4,850,358 | 7/1989 | Millar | 128/637 |
| 5,226,423 | 7/1993 | Tenerz et al. | 128/673 |
| 5,404,753 | 4/1995 | Hecht et al. | 73/204.22 |
| 5,447,073 | 9/1995 | Kalinoski | 73/861.24 |
| 5,526,696 | 6/1996 | Cappi | 73/861.95 |
| 5,692,510 | 12/1997 | Gordon et al. | 73/861.95 |
| 5,873,835 | 2/1999 | Hastings et al. | 600/488 |
| 5,957,912 | 9/1999 | Heitzmann | 600/561 |

FOREIGN PATENT DOCUMENTS

97/27802  8/1997  WIPO .

*Primary Examiner*—Harshad Patel
*Attorney, Agent, or Firm*—Foley & Lardner

[57] ABSTRACT

A system and method for measuring flow of a fluid flowing in a narrow channel. A sensor is provided, having an element sensitive to pressure, and an element sensitive to a selected chemical or physical property, both arranged at the distal end of a guide wire, for registering pressure values and values of said selected chemical or physical property. The sensor is located at a point of measurement in the narrow channel. A bolus of liquid having a property distinguishable from the selected property of the flowing fluid and detectable by the second sensitive element is injected into the fluid, and registered with said first sensitive element is a pressure pulse resulting from said injecting step. A point in time of the pulse is taken as a starting point for measuring elapsed time. Registered with the second sensitive element is the distinguishable property of the bolus in the fluid when the bolus in the fluid passes the second sensitive element. The elapsed time from the injecting of the bolus, up to the registering of the distinguishable property is noted, and a flow parameter is calculated on the basis of a value of the registered pressure pulse and a value of the distinguishable property.

22 Claims, 3 Drawing Sheets

METHOD OF FLOW MEASUREMENTS

FIELD OF THE INVENTION

This invention relates to flow measurements in narrow channels in general, and in particular to in vivo flow measurements in blood vessels.

It also relates to a system for performing such measurements.

BACKGROUND OF THE INVENTION

In order to measure flow in very narrow channels such as blood vessels, it has been known for a long time to employ a number of different methods, e.g. the so called timed venous collection technique, electromagnetic flow measurements, epicardial ultrasonic flow velocity measurement, the thermo-dilution technique, and other techniques. For details on these techniques, reference is made to "Maximal Myocardial Perfusion as a Measure of the Functional Significance of Coronary Artery Disease", by N. H. J. Pijls, (1991), Cip-Gegevens Koninklijke Bibliotheek, den Haag, (ISBN 90-9003818-3).

The present invention concerns improvements in the operation of the thermodilution principle, and therefore this principle will be briefly summarized below.

Application of the thermodilution principle in the coronary sinus was introduced by Ganz (Ganz et al, "Measurement of coronary sinus blood flow by continuous thermodilution in man, *Circulation* 44:181–195, 1971). A small catheter is introduced deeply into the coronary sinus and cold saline is delivered at its tip. Theoretically, flow can be calculated from the changes in blood temperature, registered by a thermistor close to the outlet of the coronary sinus. An advantage of this method is that only right heart catheterization is required.

The principle of thermo-dilution involves injecting a known amount of cooled liquid, e.g. physiological saline in a blood vessel. After injection the temperature is continuously recorded with a temperature sensor attached to the tip of a guide wire that is inserted in the vessel. A temperature change due to the cold liquid passing the measurement site, i.e. the location of the sensor, will be a function of the flow.

There are various methods of evaluating the temperature signal for diagnostic purposes. Either one may attempt to calculate the volume flow, or one may use a relative measure, where the flow in a "rest condition" is compared with a "work condition", induced by medicaments.

The latter is the simpler way, and may be carried out by measuring the width at half height of the temperature change profile in the two situations indicated, and forming a ratio between these quantities.

Another way of obtaining a ratio would be to measure the transit time from injection and until the cold liquid passes the sensor, in rest condition and in work condition respectively.

The former method, i.e. the utilization of the volume flow parameter as such, requires integration of the temperature profile over time in accordance with the equations given below:

$$Q_{rest} = V \bigg/ \int_{t_0}^{t_1} (T_{r,m}/T_{r,1}) dt \propto V \bigg/ \int_{t_0}^{t_1} (T_{r,0} - T_{r,m}) dt \quad (1)$$

$$Q_{work} = V \bigg/ \int_{t_0}^{t_1} (T_{w,m}/T_{w,1}) dt \propto V \bigg/ \int_{t_0}^{t_1} (T_{w,0} - T_{w,m}) dt \quad (2)$$

wherein

V is the volume of injected liquid $T_{r,m}$ is the measured temperature at rest condition $T_{r,1}$ is the temperature of injected liquid at rest condition $T_0$ is the temperature of the blood, i.e. 37° C.

$T_{w,m}$ is the measured temperature at work condition $T_{w,1}$ is the temperature of injected liquid at work condition Q is the volume flow These quantities may be used directly for assessment of the condition of the coronary vessels and the myocardium of the patient, or they may be ratioed as previously to obtain a CFR, i.e. $CFR = Q_{work}/Q_{rest}$.

The latter method, i.e. determination of the transit time requires an accurate time measurement, in view of the relatively small distances in question, about 10 cm or less from injection to measurement site.

E.g. in order to obtain a correct measurement, the time has to be measured with some accuracy. Using a simple stop watch, which is a common means of timing, is far too inaccurate for obtaining reliable transit times.

The flow F may be obtained as follows, which is a derivation for a similar technique, namely the indicator dilution technique. This is based on a rapidly injected amount of some kind of indicator, the concentration of which is measured.

For this purpose, the function h(t) is introduced which is the fraction of indicator, passing per unit of time at a measurement site at time t. In other words, h(t) is the distribution function of transit times of the indicator particles. If it is assumed that that flow of the indicator is representative for flow of the total fluid (complete mixing), h(t) is also the distribution function of transit times of all fluid particles. Suppose the total volume of fluid is made up of a very large number of volume elements $dV_i$ which are defined in such a way that $dV_i$ contains all fluid particles present in the system at t=0, with transit times between $t_i$ and $t_{i+1}$. The fraction of fluid particles requiring times between $t_i$ and $t_{i+1}$, to pass the measurement site, is $h(t_i) \cdot \Delta t$ by definition, and because the rate at which the fluid particles pass at the measurement site, equals F, the rate at which the particles making up $dV_i$ pass at the measurement site is $F \cdot h(t_i) \cdot \Delta t$. The total volume of $dV_i$ equals the time $t_i$, required for all particle segments in $dV_i$ to pass at the measurement site multiplied by the rate at which they leave. In other words:

$$dV_i = t_i \cdot F \cdot h(t_i) \cdot \Delta t$$

and by integration:

$$V = F \int_0^\infty t \cdot h(t) dt$$

The integral in the equation above represents the mean transit time $T_{mn}$, which is the average time, needed by one particle to travel from an injection site to a measurement site. Therefore:

$$V = F \cdot T_{mn}$$

or:

$$F = V/T_{mn}; \quad T_{mn} = V/F$$

which states the fundamental fact that flow equals volume divided by mean transit time.

Although the above derivation was made for the mentioned indicator dilution technique, the result is the same for thermo-dilution since the same distribution function may be employed.

RELATED PRIOR ART

Applicant's own International Patent Application WO 97/27802 entitled "Combined flow, pressure and temperature sensor", and filed Jan. 30, 1997, discloses a combined pressure, temperature and flow sensor. Therein, the utility of the claimed sensor is discussed in terms of application of the hot anemometer technique, and the thermo-dilution technique.

However, the time measurement is triggered by the cold saline passing a temperature sensor at a point upstream of the measurement point. This requires a special guide catheter provided with a temperature sensor.

SUMMARY OF THE INVENTION

Thus, the present invention seeks to provide a method and a system of determining a flow parameter utilizing the thermo-dilution principle, based on an accurate measurement of the transit time from injection up to a point of measurement.

This is achieved by making use of a pressure signal registered by a pressure sensor at a point of measurement on a location remote from the injection site, e.g. the measurement point.

Embodiments of the invention comprise selecting different triggering points of the pressure signal response for initiating the time measurement, as well as selecting different points on the temperature response curve to calculate a transit time.

The invention will now be described in closer detail with reference to the drawings.

DETAILED DESCRIPTION OF THE PREFERRED EMBODIMENT AND BEST MODE OF OPERATION

For the purposes of the present application the term "sensor" shall be understood to mean an integral unit, an assembly of separate sensing elements, or even physically separate sensing elements, however located in the vicinity of each other. In particular, but not limited thereto, such a "sensor" is mounted at the distal tip of a guide wire, or in the distal region of such guide wire.

The invention will now be described by way of example when used in a measurement of blood flow in a coronary blood vessel. However, it is to be understood that the invention is not limited to such applications, but may in fact be employed for any flow measurements, e.g. in other medical fields, as well in non-medical fields.

Figure 1:
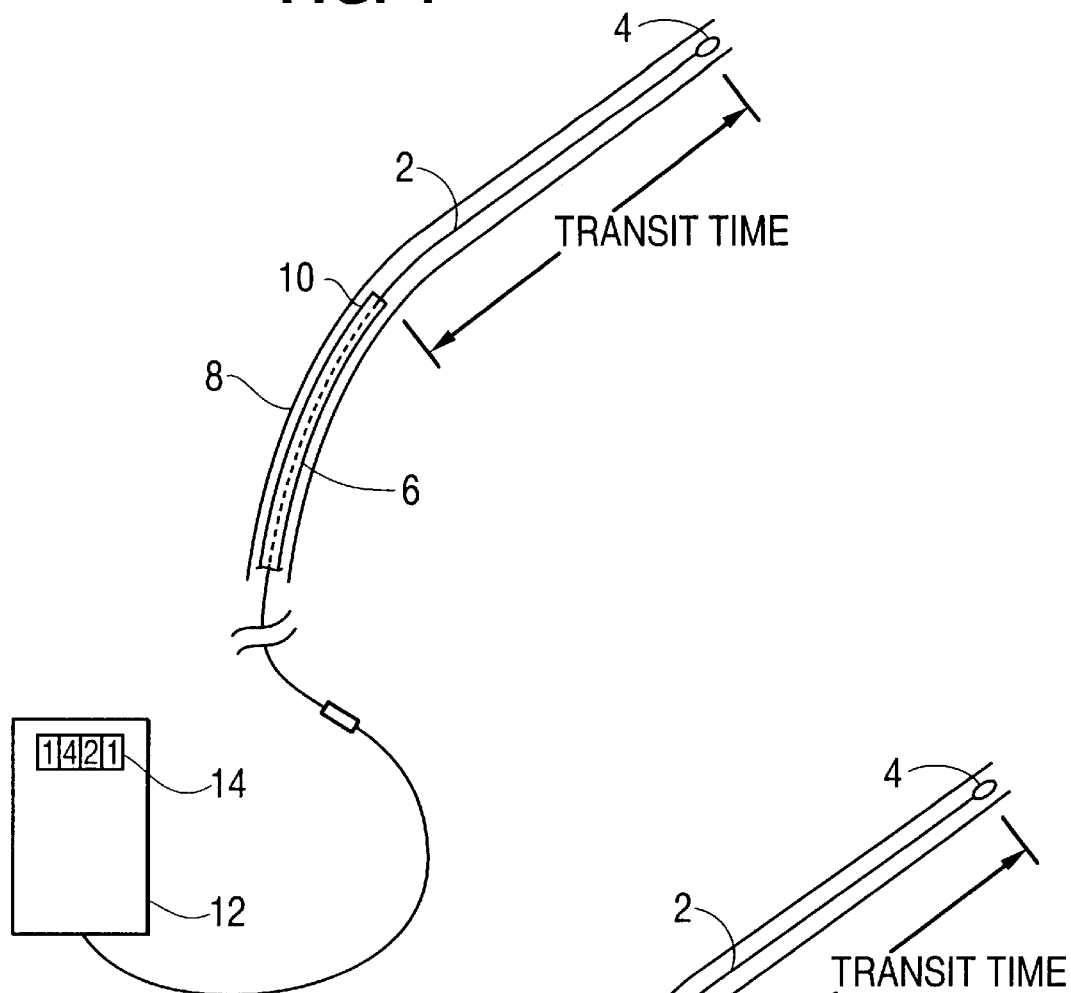
FIG. 1 shows schematically a set-up according to WO 97/27802 for measuring transit time by using a temperature sensor for triggering time measurement.

The schematically illustrated set-up in FIG. 1, which is according to WO97/27802, comprises a guide wire 2 having a combined pressure and temperature sensor 4 mounted at the distal tip. The guide wire is inserted in a guide catheter 6 and the entire assembly is located inside a coronary blood vessel 8.

The guide catheter 6 is at its distal end near the opening of the lumen, provided with a temperature sensor 10. The outputs from the respective sensors are coupled to a control unit 12 comprising electronic circuitry and software for control purposes and for performing calculations, using the theory discussed previously.

When a thermo-dilution measurement is to be performed, the guide catheter 6 is filled entirely all the way up to the distal opening with cold saline, e.g. at a temperature say 10° C. lower than the blood temperature (normally about 37° C.). The temperature is not critical, although it must be enough different from the blood temperature that an adequate gradient be registered. Preferably the temperature of the cold saline is 4–10° C. Then, a small bolus amount, e.g. 0.1 to 5 ml, preferably 0.1 to 2 ml, most preferred 0.1 to 0.5 ml, depending on blood flow, distance between injection and measurement, is injected into the guide catheter 6, normally at the proximal end. Thereby a corresponding amount will be expelled from the distal opening of the guide catheter and into the blood vessel, and will thereby be transported towards the measurement point by the flowing blood. When the cold saline passes the temperature sensor 10 on the distal tip of the guide catheter, the temperature sensor registers a temperature gradient and in response thereto a timer 14 in said control unit 12 is initiated. Again, when the bolus of cold saline passes the sensor 4 at the distal tip of the guide wire, a temperature gradient is recorded and the software in the control unit 12 processes the recorded data and outputs as a result a value of a flow parameter.

Figure 2:
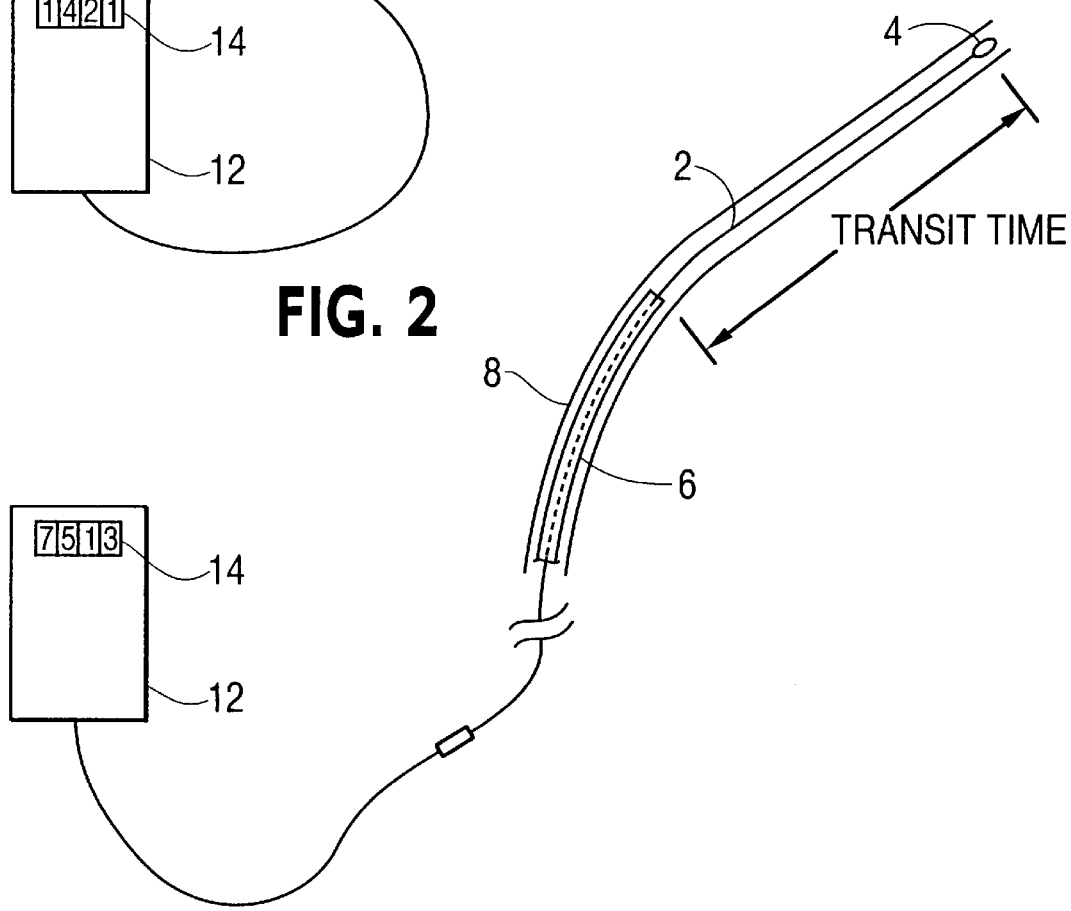
FIG. 2 shows schematically a set-up according to the invention.

In FIG. 2 a set-up according to the invention is illustrated. Elements corresponding to elements in FIG. 1 are given the same reference numerals. Here, in accordance with the invention, the temperature sensor 10 on the guide catheter 6 has been eliminated, and instead the combined sensor 4 is used for registering the injection. This is possible because the pressure pulse caused by the injection travels with the speed of sound in the flowing fluid, which for the purposes of the present invention means that the registration may be regarded as occurring at the same time as the injection.

The output from the sensor 4 at the time of injection will be registered by the control unit 12, and the timer is started.

Otherwise the method is performed in the same way as the method described above in connection with FIG. 1.

When the bolus dose of saline reaches the sensor 4 at the tip of the guide wire, the temperature gradient will be recorded and processed by the control unit software to produce the desired flow parameter.

In one embodiment the mean transit time may be calculated as discussed previously herein, by integrating the distribution function over time.

Alternatively, it is possible to use the peak value $T_{peak}$ of the temperature gradient as the relevant flow parameter.

Figure 3:
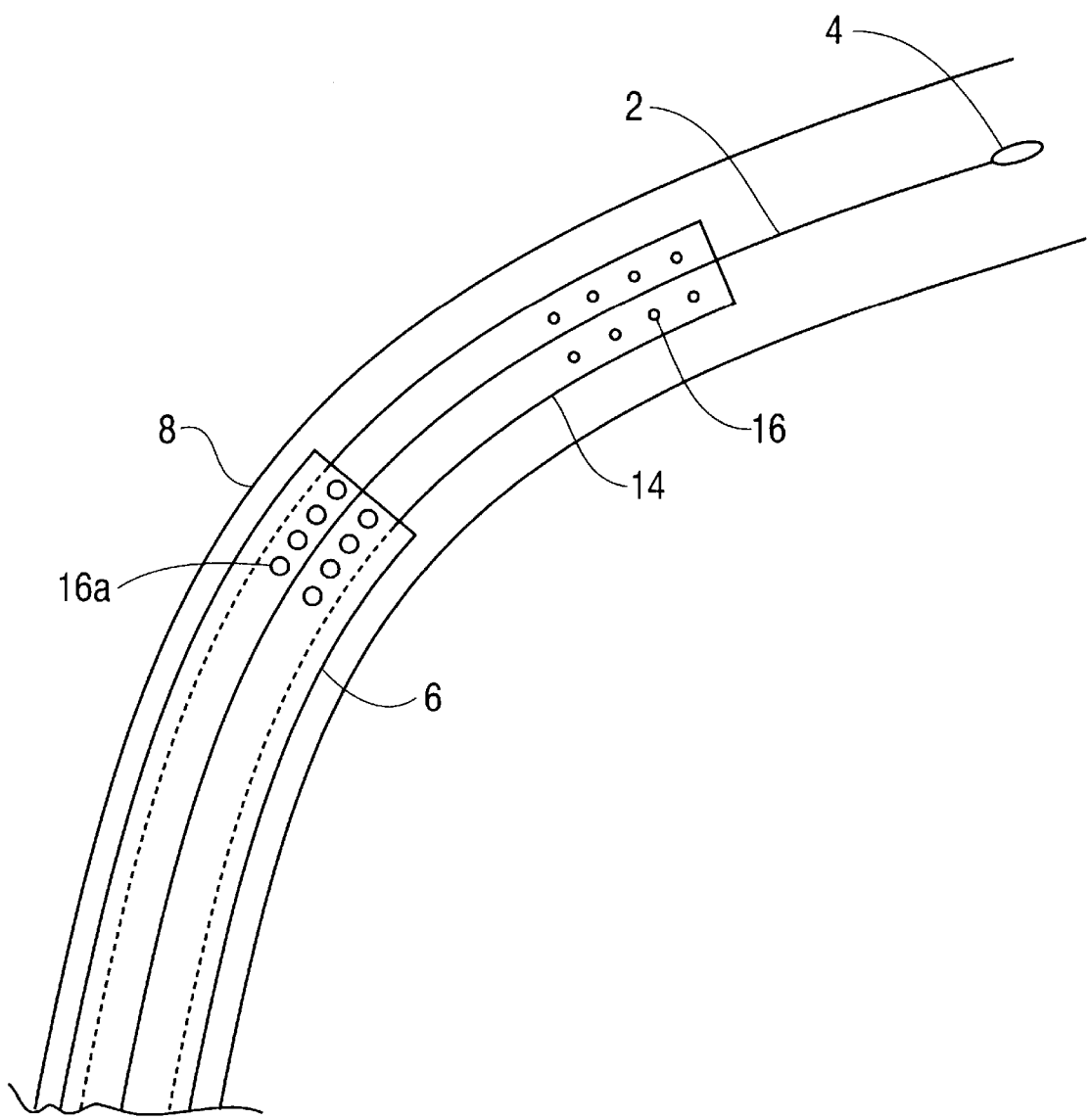
FIG. 3 illustrates an alternative embodiment of the system according to the invention.

In an alternative embodiment of performing the method, the injection of saline could be made from an auxiliary catheter 14 (see FIG. 3), that has been inserted inside the guide catheter 6, but over the guide wire 2. The advantage of this is the following. Namely, if the sensor is located in a side branch, and there are other side branches diverting from the flow path in the vessel from the distal opening of the guide catheter and the sensor, these side branches would influence the actual transit time for liquid flowing in the vessel. Thus, the accuracy of a measurement will become worse. By providing the auxiliary catheter, it becomes possible to select a point of injection that will be located such that interfering side branches are eliminated.

Also in this case, the lumen of the auxiliary catheter would be filled up to the distal opening, and then an injection would be made at the proximal end, thereby expelling liquid from the distal opening. In a preferred embodiment the auxiliary catheter is provided with side holes 16 in the distal end, in order that the injection be similar to a "shower". Of course also the guide catheter may be provided with side holes (such as 16a in FIG. 3) in the case where no auxiliary catheter is used.

Preferably the distances that the bolus of cold saline will travel should be selected in consideration of blood flow etc., such that the calculated mean transit time, $T_{mn}$, amounts to about at least 1 second and up to as much as perhaps 10 seconds. Shorter distances will give larger relative errors in the time measurement. The reason is that a measured $T_{mn}$ should be longer than one heart cycle, which normally is 1 second or more.

Figure 4:
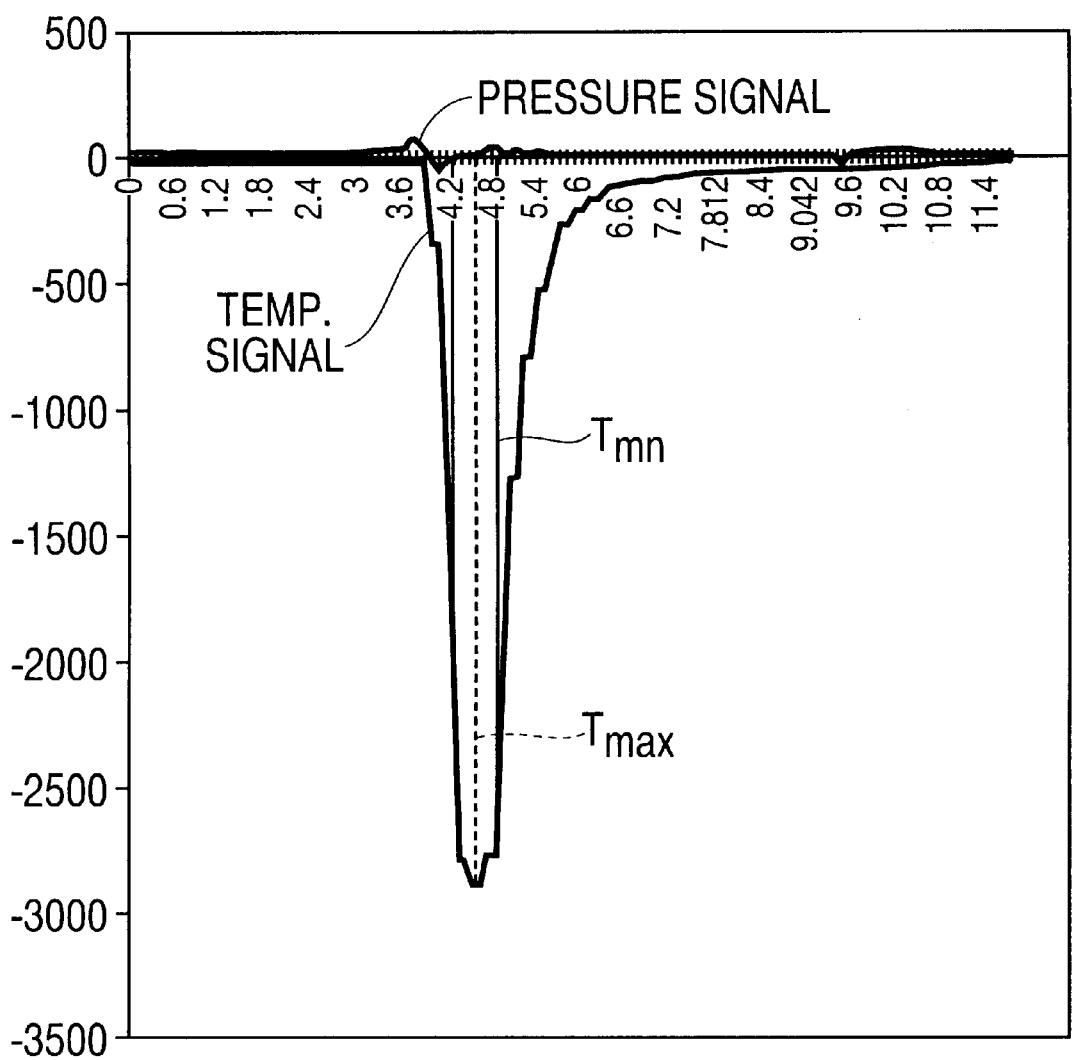
FIG. 4 shows graphs of the temperature distribution at the measurement site as a function of time.

In FIG. 4 a graph of an actual measurement is illustrated. Both the recorded pressure signal and the recorded temperature gradient are shown on the same chart recorder strip.

In one embodiment the onset of the pressure signal triggers the timer to start measuring elapsed time, at 3.6 on the time scale. The calculated $T_{mn}$ in this case equals 1.3 seconds, and is indicated with a vertical line in the graph. The onset may of course be defined in various ways. One could take the onset as a deviation from the baseline of a certain percentage, e.g. 10%. This percentage is of course to be adapted to a given situation, and can be varied in relatively wide limits.

Other possibilities are available too. For example it is also conceivable to use the maximum or peak value of the signal to trigger the time measurement.

Depending on the form of injection, the pressure signal may have different profiles. A very rapid injection would yield an extremely narrow peak, and in this case the maximum peak value is most suitable.

Other forms of injection yields a "square" signal, with a relatively well defined positive and negative flank. In this case the mid-point value of the signal may be taken as starting point for the measurement. This type of pulse will be obtained if a larger dose is injected relatively slowly at a constant flow and over a period of time, say 0.5 to 2 seconds.

In order to improve accuracy, two or more consecutive measurements can be performed within a very short time scale, on the order of seconds or tenths of seconds. This is particularly important if the measured $T_{mn}$ is close to the duration of one heart cycle.

The method of determining a flow parameter with an improved accuracy of the time measurement, is suitable for the determination of the so called Coronary Fractional Reserve (CFR). This has been discussed in applicant's own application cited above (WO 97/27802). Therein the so called hot anemometer technique was used for determining a flow parameter Q in rest and during work, and the CFR is calculated as $$CFR=Q_{work}/Q_{rest}$$

In accordance with the present invention it is also possible to use the average transit time $T_{mn}$ for the purpose of determining CFR. Namely, since $Q \alpha V/T_{mn}$ the CFR will be $$CFR=T_{mn,rest}/T_{mn,work}$$

The invention has been described in terms of measurements of blood flow in coronary vessels. However, the skilled person will realize that the principle of using the injection pressure pulse for triggering a time measurement is applicable to many other flow measurements as well. In particular it is conceivable to utilize other physical or chemical parameters for detecting the bolus dose at the measurement point, e.g. pH, concentration of solutes such as $CO_2$, oxygen, salt, biologically active species etc. as long as the injected bolus contains some species that may be detected by a suitable detector at the measurement point.

We claim:

1. A method of measuring flow of a fluid flowing in a narrow channel, comprising the steps of:

providing a sensor having a first sensitive element sensitive to pressure, and a second sensitive element sensitive to a selected chemical or physical property, both arranged at a distal end of a guide wire, for registering pressure values and values of said selected chemical or physical property;

locating said sensor at a point of measurement in said narrow channel;

injecting, into said flowing fluid, a bolus of liquid having a property distinguishable from the selected property of said flowing fluid and detectable by said second sensitive element;

registering with said first sensitive element a pressure pulse resulting from said injecting step, and taking a point in time of said pulse as a starting point for measuring elapsed time;

registering with said second sensitive element said distinguishable property of said bolus in said fluid when at least a portion of said bolus in said fluid having said distinguishable property passes said second sensitive element;

registering the elapsed time from said injecting of said bolus of liquid having said distinguishable property, up to said registering of said distinguishable property; and calculating a flow parameter on the basis of a value of said registered pressure pulse and a value of said distinguishable property.

2. A method of measuring flow of a fluid flowing in a blood vessel, comprising the steps of:

providing a sensor having a pressure sensitive element and a temperature sensitive element, both arranged at a distal end of a guide wire, for registering pressure values and temperature values;

locating said sensor at a point of measurement in said blood vessel;

injecting, into said flowing fluid, a bolus of liquid of a temperature that differs from the temperature of said flowing fluid at a point upstream of said point of measurement;

registering with said pressure sensitive element a pressure pulse resulting from said injecting step, and taking a point in time of said pulse as a starting point for measuring elapsed time;

registering with said temperature sensitive element a temperature change in said fluid caused by said bolus in said fluid having a different temperature, when said fluid having a different temperature passes said temperature sensitive element;

registering the elapsed time from said injecting of said bolus of liquid having a different temperature, up to said registering of said temperature change;

calculating a flow parameter on the basis of said registered pressure pulse value and registered temperature value.

3. The method as claimed in claim 2, wherein said bolus has an amount in the range of 0.1 to 5 ml.

4. The method as claimed in claim 2, said guide wire being inserted in a guide catheter, and said guide catheter being filled with said liquid all the way up to its distal opening before the injecting step, and wherein said injecting step comprises injecting liquid into a proximal opening of said guide catheter, thereby expelling a portion of said liquid from the distal opening of said guide catheter into the flowing fluid flow.

5. The method as claimed in claim 4, wherein said liquid is cold saline.

6. The method as claimed in claim 2, an auxiliary catheter being inserted in a guide catheter and enclosing said guide wire, a distal opening of said auxiliary catheter being positioned at a desired point in the blood vessel, further into the blood vessel than a distal opening of said guide catheter, said auxiliary catheter being used for the injection of saline.

7. The method as claimed in claim 2, wherein a mean transit time, $T_{mn}$, is calculated as the flow parameter.

8. The method as claimed in claim 2, wherein the distance between injection of said liquid into the flowing fluid and the point of measurement is selected such that a mean transit time $T_{mn}$ is approximately at least 1 second.

9. The method as claimed in claim 2, wherein an onset of the pressure pulse is taken as the starting point for the elapsed time measurement.

10. The method as claimed in claim 9, wherein an onset of the pressure pulse is defined as percentage of deviation from a base line value.

11. The method as claimed in claim 2, wherein the pressure pulse resulting from the injection step is narrow with a well defined peak.

12. The method as claimed in claim 2, wherein the peak of said pressure pulse is taken as the starting point for said time measurement.

13. The method as claimed in claim 2, the bolus of liquid being injected into said flowing fluid through a plurality of side holes in a guide catheter at a slow enough rate that an essentially square profile of the pressure pulse is achieved.

14. The method as claimed in claim 13, wherein a mid point of the essentially square pulse is taken as the starting point for said time measurement.

15. The method as claimed in claim 13, wherein a front flank of the essentially square pulse is taken as the starting point for said time measurement.

16. The method as claimed in claim 13, wherein a rear flank of the essentially square pulse is taken as the starting point for said time measurement.

17. The method as claimed in claim 2, wherein said flow parameter is calculated as the elapsed time from the pressure pulse resulting from said injecting step up to a maximum value of said temperature change.

18. A system for measuring a flow parameter of a fluid flowing in narrow channels, comprising:

a guide wire having a distal end, and being provided with sensor means for selectively detecting pressure and another physical or chemical property of the flowing fluid, and for outputting signals representative of said pressure and other physical or chemical property;

a control unit coupled to said sensor means;

means for injecting, into said flowing fluid, a bolus amount of liquid having physical or chemical property distinguishable from a property of said flowing fluid, for creating a pressure pulse;

timer means in said control unit which, is coupled so as to start to measure time in response to said pressure pulse detected by said sensor means;

processing means in said control unit for processing said measured time, and said signals representative of said other physical or chemical property; and means in said control unit for calculating a flow parameter on the basis of said processed signals.

19. The system as claimed in claim 18, wherein said sensor means detects pressure and temperature.

20. The system as claimed in claim 19, wherein said injecting means comprises a guide catheter having a distal opening.

21. The system as claimed in claim 20, wherein said injecting means further comprises an auxiliary injection catheter, provided inside said guide catheter and extendible from said distal opening of said guide catheter, thereby providing selectable points of injection inside said a channel.

22. A method of diagnosing small vessel disease, by performing measurements of flowing fluid at a site in a blood vessel distally of a suspected stricture, comprising the steps of:

a) providing a sensor having a pressure sensitive element and a temperature sensitive element both arranged at a distal end of a guide wire for registering pressure and temperature values;

b) locating said sensor at a point of measurement in said blood vessel;

c) injecting a bolus of liquid of a temperature that differs from the temperature of said flowing fluid at a point upstream of said point of measurement;

d) registering the pressure pulse resulting from said injecting step by said pressure sensitive element, and taking the point in time of said pulse as a starting point for measuring elapsed time;

e) registering a temperature change of said fluid caused by said injecting step when said fluid passes said temperature sensitive element;

f) registering the elapsed time from said injection of said bolus of liquid to said registering of said temperature change;

g) calculating a flow parameter $T_{rest}$ on the basis of said registered pressure and temperature values, corresponding to a rest situation;

h) injecting a vaso dilating drug in said vessel to simulate a work condition;

i) repeating the steps a) to f);

j) calculating a flow parameter $T_{work}$ on the basis of said registered pressure and temperature values, corresponding to a work situation;

k) calculating Coronary Fractional Reserve=$T_{rest}/T_{work}$; and l) comparing the calculated Coronary Fractional Reserve with a corresponding quantity representative of a healthy patient.

* * * * *